(12) United States Patent
Vinci

(10) Patent No.: US 7,914,049 B2
(45) Date of Patent: Mar. 29, 2011

(54) HYDRAULIC CONNECTOR AND A HYDRAULIC CIRCUIT INCORPORATING THE CONNECTOR

(75) Inventor: Luca Vinci, Poggio Rusco (IT)

(73) Assignee: Gambro Lundia AB, Lund (SE)

( * ) Notice: Subject to any disclaimer, the term of this patent is extended or adjusted under 35 U.S.C. 154(b) by 303 days.

(21) Appl. No.: 12/280,942

(22) PCT Filed: Mar. 2, 2006

(86) PCT No.: PCT/IB2006/000450
§ 371 (c)(1),
(2), (4) Date: Aug. 27, 2008

(87) PCT Pub. No.: WO2007/099386
PCT Pub. Date: Sep. 7, 2007

(65) Prior Publication Data
US 2009/0001718 A1    Jan. 1, 2009

(51) Int. Cl.
*F16L 21/00* (2006.01)

(52) U.S. Cl. .................. 285/235; 285/179; 285/133.11; 604/4.01

(58) Field of Classification Search .................. 285/235, 285/236, 237, 179, 133.11, 417; 604/4.01
See application file for complete search history.

(56) References Cited

U.S. PATENT DOCUMENTS

| | | | | |
|---|---|---|---|---|
| 1,180,733 A | * | 4/1916 | Mulherin | 285/235 |
| 2,261,948 A | * | 11/1941 | Beach | 285/236 |
| 3,127,892 A | * | 4/1964 | Bellamy, Jr. et al. | 285/235 |
| 3,945,617 A | * | 3/1976 | Callery | 285/235 |
| 4,109,097 A | * | 8/1978 | Berry | 285/235 |
| 4,238,059 A | * | 12/1980 | Caraway et al. | 285/417 |
| 4,381,591 A | * | 5/1983 | Barger et al. | 285/235 |
| 4,541,657 A | | 9/1985 | Smyth | |
| 4,657,285 A | | 4/1987 | Akiyama et al. | |
| 4,684,672 A | | 8/1987 | Buchanan et al. | |
| 4,803,053 A | * | 2/1989 | Williamson | 285/235 |
| 4,810,008 A | * | 3/1989 | Brodie | 285/235 |
| 4,850,984 A | * | 7/1989 | Harris | 285/235 |
| 4,905,736 A | | 3/1990 | Kitami et al. | |
| 4,991,882 A | | 2/1991 | Gahwiler | |
| 5,218,875 A | * | 6/1993 | Volpe et al. | 285/235 |
| 5,267,757 A | | 12/1993 | Dal Palu | |
| 5,536,258 A | | 7/1996 | Folden | |
| 5,591,251 A | * | 1/1997 | Brugger | 95/242 |
| 5,637,102 A | * | 6/1997 | Tolkoff et al. | 285/417 |
| 5,693,025 A | | 12/1997 | Stevens | |
| 5,770,064 A | | 6/1998 | Jonsson et al. | |

(Continued)

FOREIGN PATENT DOCUMENTS
EP    0579916    1/1994
(Continued)

*Primary Examiner* — David E Bochna
(74) *Attorney, Agent, or Firm* — Pearne & Gordon LLP

(57) ABSTRACT

A hydraulic connector made entirely of an elastomeric material connects tubes or other hydraulic circuit components used in machines for extracorporeal blood treatment. The hydraulic connector comprises a main body (2), which defines a conduit (3), and a predetermined number of protuberances (6) fashioned to enable a stable engagement of the connector to an end of a tubular port (7) of tubing or other hydraulic component. The conduit (3) exhibits a first longitudinal portion (3a) directed along a first development axis (9) and a second longitudinal portion (3a) directed along a second development axis (10); the axes (9, 10) do not coincide.

21 Claims, 5 Drawing Sheets

U.S. PATENT DOCUMENTS

| | | | |
|---|---|---|---|
| 5,782,808 A | 7/1998 | Folden | |
| 5,860,677 A | 1/1999 | Martins et al. | |
| 6,152,495 A | 11/2000 | Hoffmann et al. | |
| 6,602,090 B2 | 8/2003 | Kato | |
| 6,821,267 B2 | 11/2004 | Veillon et al. | |
| 7,166,084 B2 * | 1/2007 | Utterberg | 604/4.01 |
| 7,291,123 B2 * | 11/2007 | Baraldi et al. | 604/6.16 |
| 7,540,958 B2 * | 6/2009 | Chevallet et al. | 210/258 |
| 7,559,911 B2 * | 7/2009 | Giannella | 604/6.15 |
| 7,780,621 B2 * | 8/2010 | Neri et al. | 604/6.15 |
| 2003/0171719 A1 | 9/2003 | Veillon et al. | |

FOREIGN PATENT DOCUMENTS

| | | |
|---|---|---|
| EP | 0645161 | 3/1995 |
| EP | 0 747 074 A1 | 12/1996 |
| EP | 0753323 | 1/1997 |
| EP | 0753697 | 1/1997 |
| EP | 0 944 795 A1 | 9/1999 |
| EP | 1262703 | 12/2002 |
| EP | 1 355 099 A1 | 10/2003 |
| EP | 1527797 | 5/2005 |
| FR | 2 513 884 A1 | 4/1983 |
| FR | 2700379 | 7/1994 |
| GB | 860 906 A | 2/1961 |
| GB | 2045883 | 11/1980 |
| GB | 2 110 564 A | 6/1983 |
| GB | 2 244 671 A | 12/1991 |
| GB | 2261376 | 5/1993 |
| WO | WO9521648 | 8/1995 |
| WO | WO9641092 | 12/1996 |
| WO | 98/28565 A1 | 7/1998 |
| WO | WO 9828565 | 7/1998 |
| WO | WO9936009 | 7/1999 |
| WO | WO03076002 | 9/2003 |

* cited by examiner

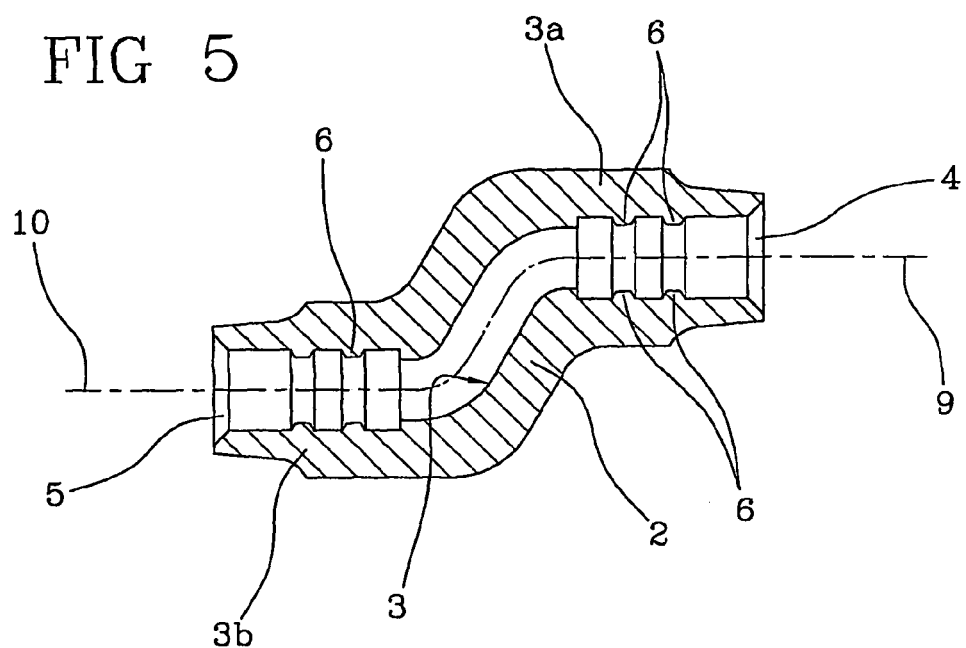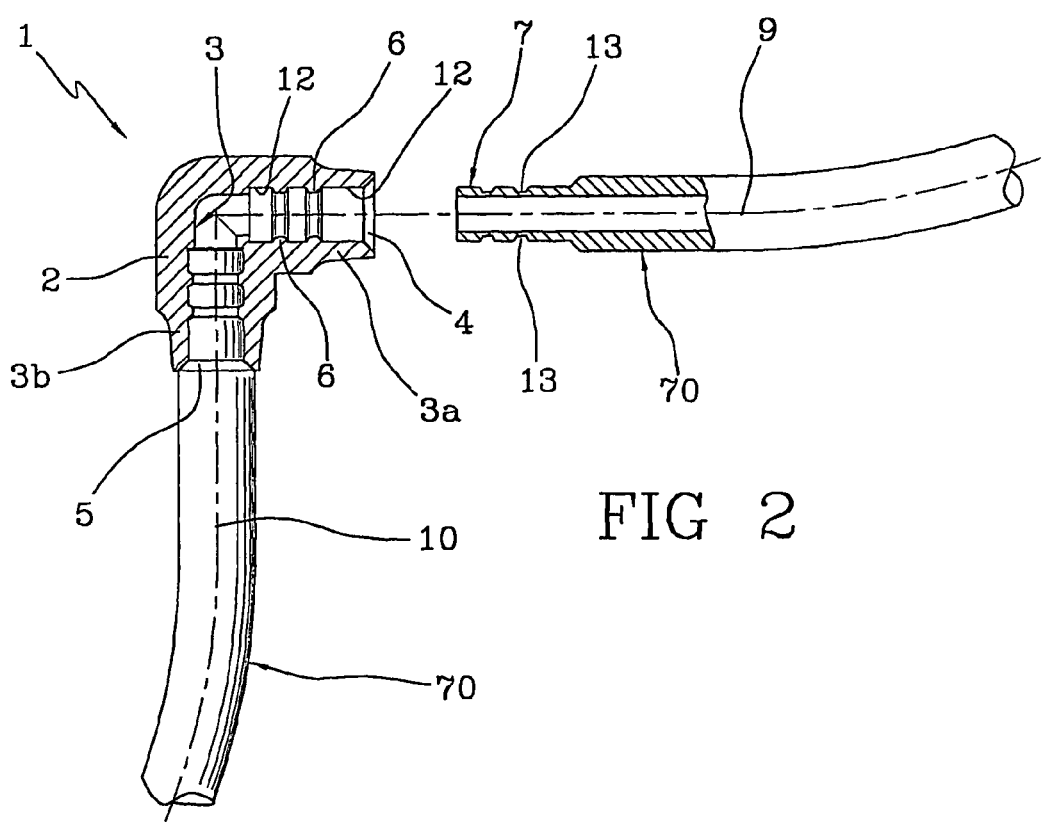

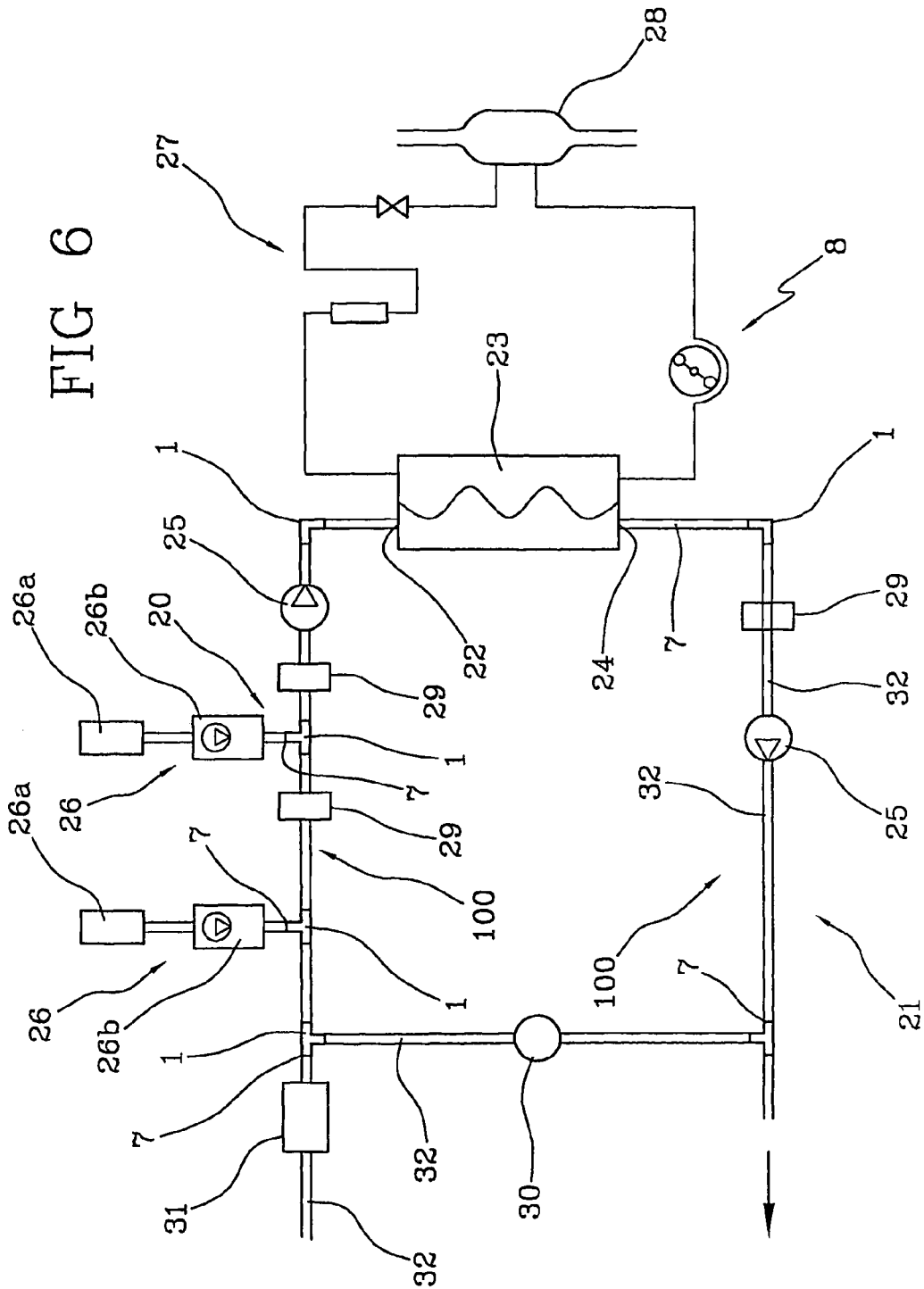

HYDRAULIC CONNECTOR AND A HYDRAULIC CIRCUIT INCORPORATING THE CONNECTOR

TECHNICAL FIELD

The invention relates to a hydraulic connector made of an elastically deformable material, destined to place in communication a predetermined number of components belonging to a hydraulic circuit, which connector is advantageously usable in medical applications such as machines for extracorporeal blood treatment.

BACKGROUND ART

As is known, medical devices at present in use for treatment of kidney problems, and especially for extracorporeal blood treatment, are constituted by complex apparatus which internally comprise hydraulic circuits for managing the various patient treatment operations.

By way of mere non-exhaustive example, dialysis machines at present in use comprise a blood circuit destined to remove blood from the patient and to bring it to a treatment unit. Once treated the blood is returned to the patient. In general, the above-described circuit is accompanied by a preparation line of a treatment fluid which brings a dialyser liquid into a situation of exchange with the blood inside the treatment unit, the exchange enabling an interaction between dialyser liquid and blood so as to achieve the desired treatment effect.

Apart from the above-mentioned blood line and dialyser liquid preparation line, there might also be circuits destined to enable effecting of preparation of other liquids, such as medical or replacement liquids, as well as further circuits or lines for discharging the used liquid, for the control of ultrafiltration, or other lines, safety lines and/or washing lines which further increase the complexity and number of circuits internally of the machine. Each medical device for dialysis operations internally comprises a plurality of tubes and connections for the tubes, destined for transporting fluids of varying natures and under different flow and pressure conditions which are also variable over periods of time.

The presence of electronic apparatus for management and control, as well as motors and moving mechanical parts in the machines means that the problem of sealing and reliability of the hydraulic circuits is seen to be of particular and primary importance.

Clearly the most critical area in the hydraulic plants is the connections present in the actual fluid lines.

At present, usual dialysis machines, to join two or more tubes, use connections made of elastomeric materials, such as, for example, silicone. Generally these connectors are constituted by a main body internally affording a channel which the fluid crosses.

The tubes are directly connected to the connectors and the connector joints are achieved by friction coupling. The friction forces generated between the smooth internal surface of the connector and the tube are strong enough to guarantee fluid seal and mechanical seal of the hydraulic circuit.

This type of connector, though widespread in use in the sector, is however subject to improvement under certain of its aspects.

Firstly, an important observation is that hydraulic circuits in dialysis machines are subject to high quantities of fluid flow.

Generally speaking the movement of the fluid is obtained, in this type of machine, by using pumps, for example gear pumps or peristaltic pumps, which by their nature create non stationary flow conditions inside the hydraulic circuit; the flows produced are characterised by the presence of series of repeated and successive pressure peaks, which can also be non-cyclic in nature.

The particular types of treatment to be performed, but also the washing and sterilising operations on the circuits themselves, lead to flow conditions inside the circuitry which are such as to generate considerable stress thereon, especially at the connections and especially when flow is inverted.

Because of the above, it is not an infrequent occurrence that after repeated cycles the tube end portions can detach from the connectors, causing exit of liquids contained therein.

This can lead to serious problems during treatment of a patient, but can also have dire consequences for the electrical or electronic apparatus which the machine is equipped with.

Document EP645161 describes a variable-section straight connector having removable portions for connecting tubes having different diameters.

Document EP 1262703 teaches a connector for non-medical use devices which connects coaxial tubes having different sections. The connector is provided with ribbing at the connecting ends.

Furthermore it is obvious that even simple changes in relative positions between the tube and the connector can lead to an imperfect fluid seal, with the attendant risk that fluid can leak out and damage the apparatus.

SUMMARY OF THE INVENTION

Given the above situation, the technical aim of the present invention is to resolve the drawbacks in the cited prior art.

A first aim of the invention is to make available a connector for hydraulic circuits which can be used in medical machines and which offers optimal mechanic seal and fluid seal for fluids which are not in stationary flow conditions, and in particular in the presence of sometimes sharp variations in flow direction across the connector.

A further aim of the invention is to separate the mechanical fluid seal function from the mechanic seal function in such a way as to optimise both.

Additionally, an aim of the invention is to make available a connector that can be made with complex configurations, without losing anchoring and seal efficiency.

Accessory aims of the present invention are therefore to realise an extremely simple product having comparable overall costs to those for connectors at present in use, which do not lead to special problems of assembly and use. These and other aims, which will better emerge during the course of the present description, are attained by a hydraulic connector, a hydraulic circuit and a machine for extracorporeal blood treatment incorporating the connector, according to what is described in the appended claims.

Further characteristics and advantages will better emerge from the detailed description that follows of a preferred but not exclusive embodiment of a hydraulic connector according to the present invention.

DETAILED DESCRIPTION

The description will be made with reference to the accompanying figures of the drawings, provided by way of non-limiting example, in which:

FIG. 2 shows the connector in a coupled connection with a port of a tube;

FIG. 5 is a possible further embodiment of the connectors of the invention;

FIG. 6 is an extremely schematic view of a machine for extracorporeal blood treatment in which the connector and the hydraulic circuit of the invention can be used.

Figure 1:
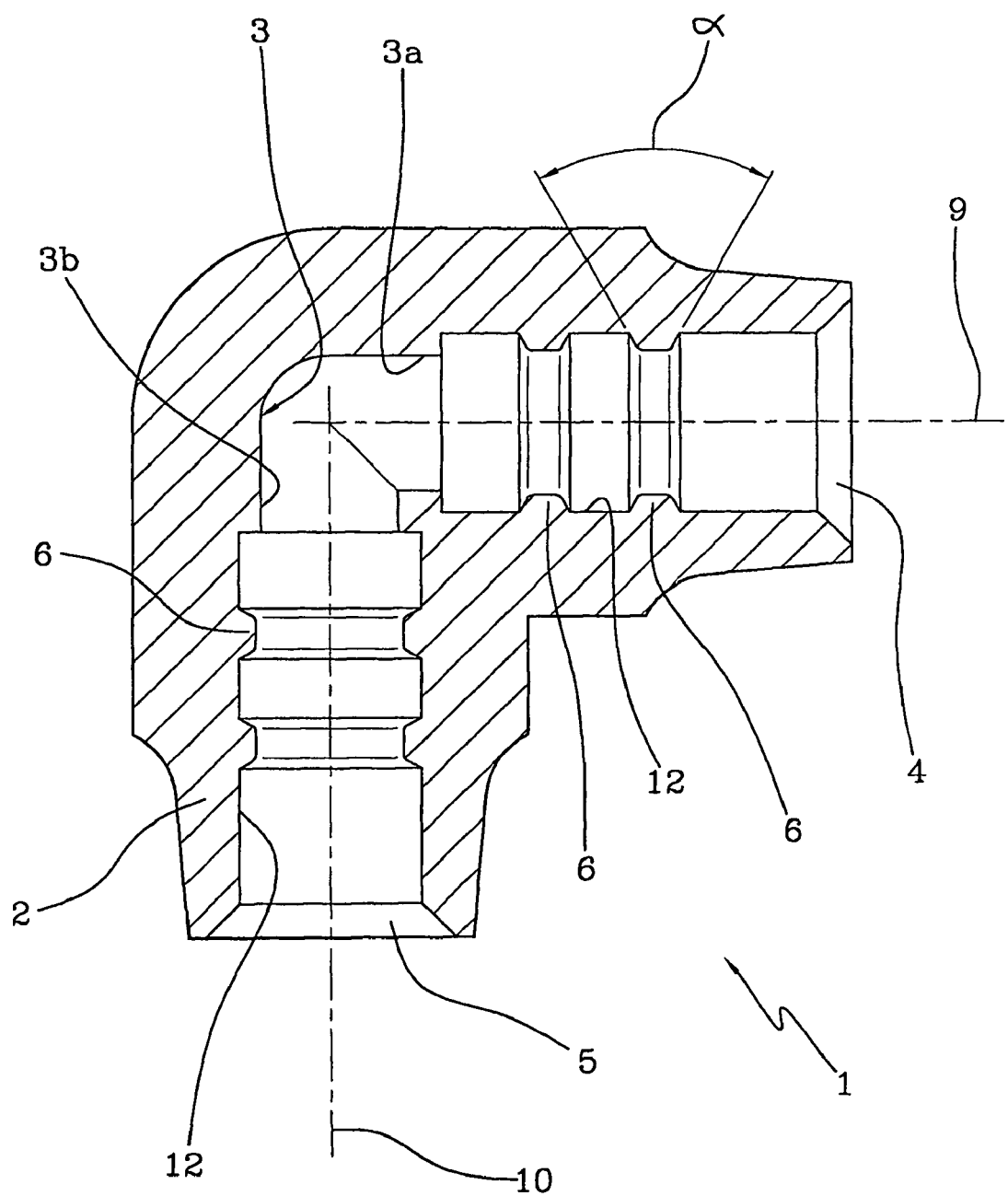
FIG. 1 is a section of the hydraulic connector of the invention.

With reference to the figures of the drawings, 1 denotes in its entirety a hydraulic connector made of an elastically deformable material. The connector is usable for connecting terminal tube ports or tubular ports in inlet and/or outlet of other hydraulic components 70 such as, for example, pumps, fluid parameter sensors, filters, ultrafilters, fluid treatment units, valves or valve groups, etc.

As can be noted from the accompanying figures of the drawings, the connector comprises a main body 2 which internally presents at least a conduit 3 for allowing passage of a fluid (for example a dialyser liquid or a washing liquid), between at least an inlet opening 4 and an outlet opening 5 in reciprocal connection across the conduit 3.

Generally, the shaped elbow conduit of the type illustrated in FIG. 1 comprises a single inlet and a single outlet, also as in the connector illustrated in FIG. 5.

Figure 4:
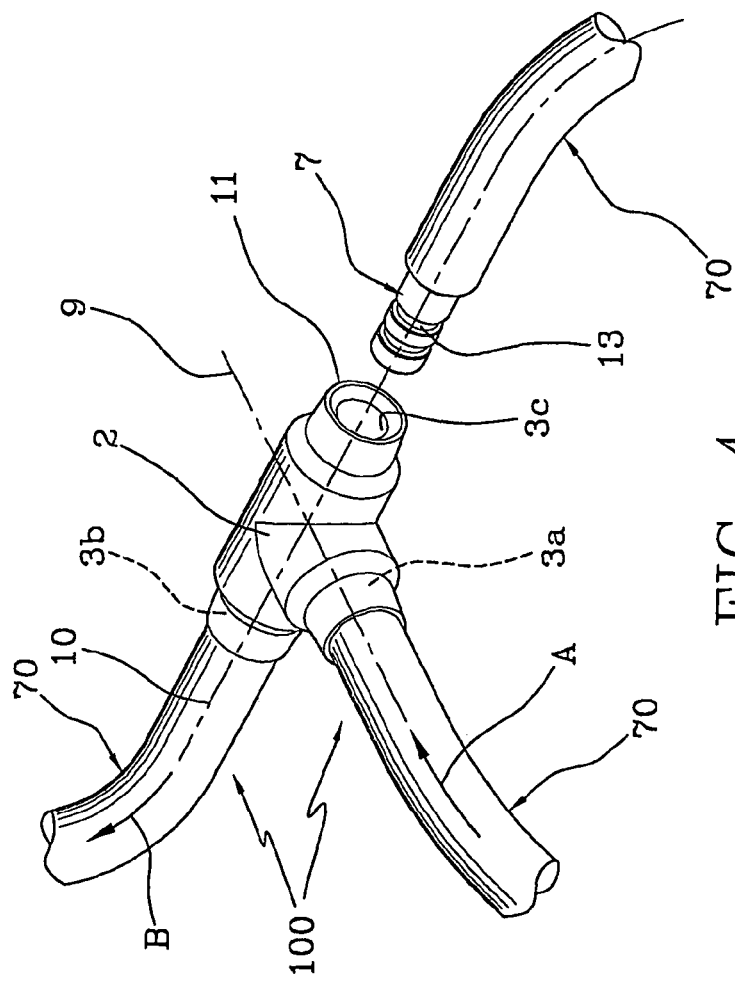
FIG. 4 illustrates a T-shaped connector of the invention.

The T-shaped connector of FIG. 4 can comprise one or more inlets, or alternatively one or more outlets.

The connector of the invention can comprise other shapes, according to the geometry and relative positions of the ports to be connected; for example, three-way connectors can be Y- or T-shaped; two-way connectors can be L- U- or S-shaped; four-way connectors can be X- or H-shaped, and so on.

The two or more inlet or outlet openings can be oriented and arranged in such a way that the connector develops three-dimensionally.

As can be seen in FIG. 1, the connector 1 is entirely and in all its parts constructed in an elastomeric material; by way of example, it could be made of silicone. The connector is made by moulding, for example by injection moulding, for example in a single mouldable elastomeric material; thanks to injection moulding the connector can advantageously be given very different geometric shapes without compromising its functionality as an anchor or its sealing performance.

As can be seen in FIGS. 1 and 2, the main body 2 comprises a predetermined number of protuberances 6 suitable for achieving a stable coupling of the main body 2 to a tubular port 7, for example a tube 70 (as in the figures) or another hydraulic component.

The protuberances 6 are fashioned internally of the conduit 3 and are located at each inlet opening 4 and at each outlet opening 5.

An excellent mechanical coupling is obtained between the port portion 7 and the connector 1 by using at least two protuberances 6 at the inlet opening 4 and the outlet opening 5.

The conduit 3 is usually defined by a through-cavity having a circular section for permitting insertion of the terminal portion of the port 7 and the consequent passage of fluid from a tube 70 to another or between a tube and another hydraulic component, or between two hydraulic components.

In each case at least an initial tract of the conduit at the inlet opening 4 and at least an initial tract of the conduit 3 at the outlet opening exhibit a transversal section, directed perpendicularly to the respective development axes 9, 10 and having a substantially circular shape; the protuberances 6 are constituted by annular projections.

The protuberances 6 exhibit a section (referring to a section plane passing through the development axes 9, 10) with a tapered trapezoid configuration having oblique sides that define between them an angle α L comprised, for example, between 30° and 90°, and in particular an angle of about 60° (see FIG. 1).

The geometry of the conduit 3 exhibits a first longitudinal portion 3a which is directed along a first development axis 9 and a second longitudinal portion 3b which is direction along a development axis 10; the first and second development axes 9, 10 are not coincident. In the example of embodiment of FIG. 5, the axes are parallel, while in the further embodiments the axes are incident; alternatively, the axes could be skewed according to the position and shape of the ports 7 which they are destined to connect.

In each case the conduit 3 develops in a non-straight path.

Figure 3:
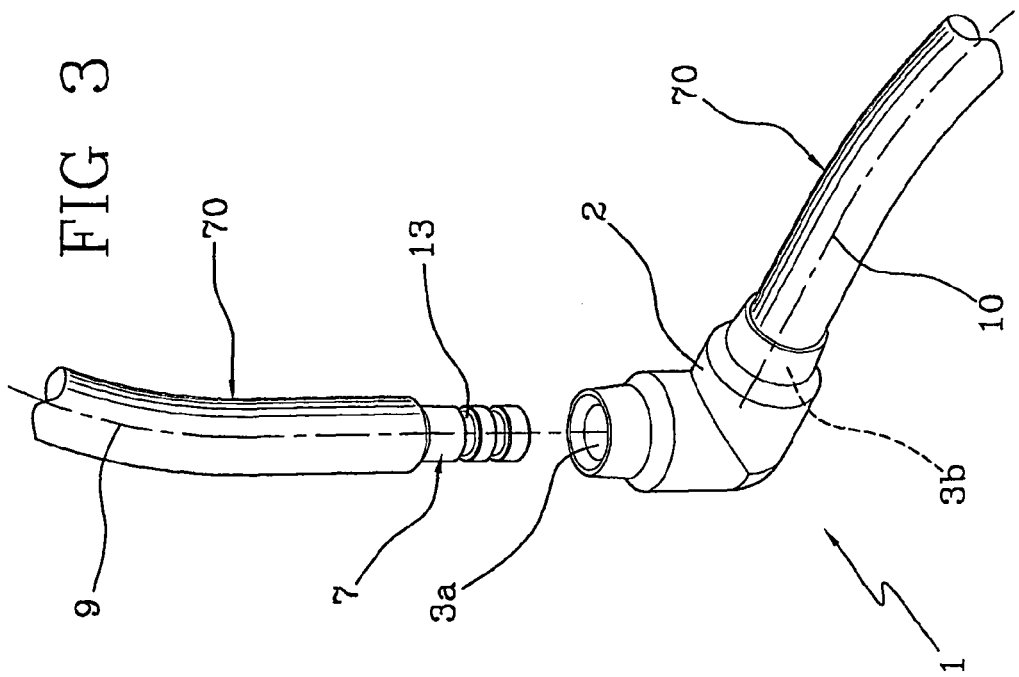
FIG. 3 is the example of FIG. 2 in perspective view.

In other words, a fluid inletting into the connector will exit therefrom after having at least once changed direction (see for example flows A and B in FIG. 4). This change of direction can also be extremely brusque, as in the case of FIG. 3, where the change is obtained in correspondence of the elbow of the connector.

It is thus extremely important for a connector made of an elastomeric material (and therefore highly deformable) and exhibiting a internal fluid pathway which is not straight and which often develops three-dimensionally to guarantee the necessary performance characteristics of mechanical connection and fluid seal.

The above is guaranteed by two distinct technical aspects.

The protuberances 6 located at the inlets and outlets are engaged by corresponding recesses 13 afforded in the port 7, so that a constraint joint is achieved which guarantees an optimal mechanical seal. The protuberances 6 are defined by annular projections which are of a smaller height (in the illustrated embodiments only a slightly smaller height) than the depth of the corresponding recesses 13.

The fluid seal is guaranteed by interference between the respective contacting surfaces, external for the tube and internal for the connector to which the tube is coupled by means of a slightly forced insertion therein.

The use of protuberances 6 and corresponding recesses 13 creates a stable coupling, as cooperation between the two elements tends to bring them into the optimal coupling position even after relative displacement caused by peaks of pressure or flow.

The stability is also aided by the presence of the tapers on the protuberances 6.

The exemplifying embodiments adopt a first and second portion 3a, 3b of the conduit which exhibit same transversal sections, so that the tubes or components 70 having ports 7 of the same diameter can be connected.

In the case of connectors having 3 or more mouths (such as for example T-connectors), obviously apart from the two portions 3a, 3b there will be a third portion 3c which ends in a further inlet/outlet zone 11.

Figure 7:
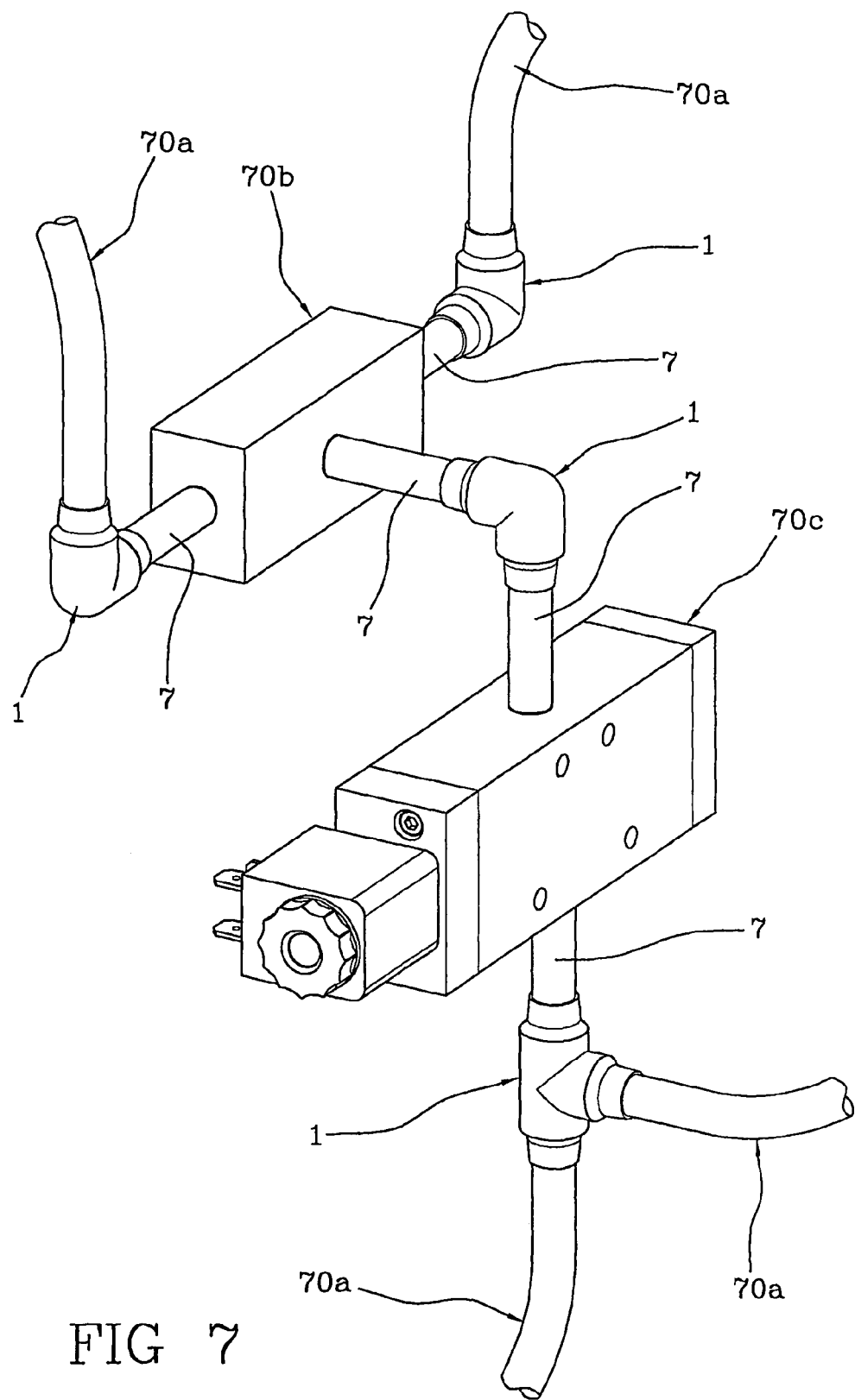
FIG. 7 is a schematic illustration of a portion of a hydraulic circuit, in which various hydraulic components are connected by connectors of the invention.

The above-described connectors are usable in hydraulic circuits of the type shown in FIG. 4, in which the connectors couple a plurality of tubes or other components 70 arranged internally of the machine in a three-dimensional spatial distribution in which the ports 7 which are to be connected are usually non-aligned, increasing the generation of mechanical stress in the connection zone between the connector and the port. For reasons of simplicity FIG. 4 shows tubes as examples of hydraulic components, but the connectors 1 can be used to connect other hydraulic components with ports 7 positioned in very varied spatial arrangement situations. For example, in FIG. 7 a portion of a hydraulic circuit is schematically shown which comprises hydraulic components such as tubes 70*a*, a three-way valve 70*b* and a pump 70*c*. The components exhibit ports 7 connected by connectors 1 according to the present invention.

The invention also relates to a hydraulic circuit especially for machines for extracorporeal blood treatment, comprising:
- a plurality of hydraulic connectors 1 of the described type;
- a plurality of hydraulic components each having one or more tubular ports 7 engaging respective ports of the connectors 1.

The hydraulic components of the circuit generally exhibit ports 7 having longitudinal axes which do not coincide, thus necessitating the use of connectors 1 which are not straight. For example, the hydraulic components comprise one or more of the following components: valves, pumps, tubes, sensors of a fluid characteristic, filters (for example ultrafilters with a semi-permeable membrane), fluid treatment units, fluid collection reservoirs, and so on.

Finally the hydraulic circuit obtained thanks to the use of the connectors 1 can advantageously be used in machines 8 for extracorporeal blood treatment where there is at least a section 20 destined for preparation of a treatment fluid and at least a section 21 destined for discharge of the used treatment fluid.

The machine (which is per se of a known type) is schematically illustrated in FIG. 6.

It can be seen how the fluid preparation section 20 comprises a hydraulic circuit 100 exhibiting a predetermined number of connectors 1 and a predetermined number of components placed in reciprocal fluid connection in order to create, treat and bring the treatment fluid to an inlet port 22 of the unit for extracorporeal blood treatment 23.

Also, the discharge section 21 is provided with a plurality of connectors 1 and a plurality of components destined to bring the fluid from an outlet port 24 of the treatment unit 23 up to the discharge.

For example, the preparation section and/or the discharge section comprises, as hydraulic components, apart from numerous tube tracts 32, at least a movement pump 25 (for example a gear pump) to generate the fluid flow across the treatment unit 23, one or more sensors 29 for measuring various parameters (pH, conductivity, temperature, flow, pressure, etc.), flow control valves 30, possibly further units 26 (concentrate containers 26*a* with a correspondingly dedicated supply pump 26*b*) for the addition of concentrates, devices 31 for treatment or control of the fluid under preparation (filters, reservoirs, heaters, flow regulators, heat exchangers, etc.) not further specified as of known type and only given as examples for the purpose of the description of the invention. Some, if not necessarily all, of the components described can be interconnected at the respective ports 1 to the connectors 1 of the invention. Obviously in the apparatus of FIG. 6 there will also be a blood line 27 predisposed to remove the blood from the patient 28 and send it in the treatment unit 23, and thereafter from the unit 23 back to the patient. It is clear that the same machine may present many other tubes and/or hydraulic components and relative connections, as well as a control system cooperating with and all mechanical, electric and electronic instrumentation. Obviously the number and arrangement of the connections 1 will be much more complex than what is illustrated in FIG. 6, which is only intended as a schematic example.

The invention offers important advantages.

The separation of the mechanical seal function and the hydraulic seal function of the various parts of the connector enables the use of connectors made exclusively of elastomeric material, which means that even with conduits of a complex type, there are no problems of leakage or disconnections.

The presence of fluid flows brusquely changing direction (see inlet A and outlet B in FIG. 4) does not cause any special seal problems for the connectors of the invention, even where there are repeated and non-cyclic pressure peaks.

Thus the device of the invention enables realisation of complex hydraulic circuits, in which the components and the relative ports 7 can be unaligned and angularly staggered to one another, as typically happens in the circuits of extracorporeal blood treatment machines.

The connectors are however simple to manufacture, easy to assemble and have relatively contained production costs.

Also possible is the realisation of hydraulic circuits or sections thereof simply by connecting together the ports of the various hydraulic components constituting the circuits, making use of the connectors 1 of the invention, which can be shaped in any way since the elastomeric material is easily moulded and even a complex connector 1 shape does not reduce the fluid seal and mechanical anchoring characteristics thereof.

The invention claimed is:

1. A hydraulic connector made of an elastically deformable material, comprising:
a main body (2) internally defining at least a conduit (3) for enabling passage of a fluid, the main body (2) exhibiting at least an inlet opening (4) and at least an outlet opening (5) which are reciprocally connected by the at least a conduit (3) in order to enable the passage of the fluid, the main body (2) further comprising a predetermined number of protuberances (6) for enabling a stable engagement of the connector (1) to a tubular port (7), wherein:
the conduit (3) exhibits a first longitudinal portion (3*a*) directed along a first development axis (9) and a second longitudinal portion (3*b*) directed along a second development axis (10), the first development axis (9) and the second development axis (10) not coinciding, and
wherein in section according to a plane passing through the first development axis (9) or the second development axis (10) the protuberances (6) exhibit a tapered trapezoid configuration, which has oblique sides forming between them an angle ($\alpha$) comprised between 30° and 90°.

2. The connector of claim 1, wherein the first development axis (9) and the second development axis (10) of the first longitudinal portion (3*a*) and the second longitudinal portion (3*b*) are reciprocally skewed or incident.

3. The connector of claim 1, wherein the protuberances (6) extend internally of the at least a conduit (3) at the at least an inlet opening (4) and the at least an outlet opening (5).

4. The connector of claim 1, wherein at least an initial tract of the at least a conduit (3), at the at least an inlet opening (4), exhibits a section which is transversal to the first development axis (9) which section is circular, the protuberances (6) being defined by annular projections.

5. The connector of claim 1, wherein at least a final tract of conduit (3) at an outlet opening (5) exhibits a section which is transversal to the second development axis (10) and is circular, the protuberances (6) being defined by annular projections.

6. The connector of claim 1, wherein at least two of the protuberances (6) are located at the at least an inlet opening (4) and at least two of the protuberances (6) are located at the at least an outlet opening (5).

7. The connector of claim 1, wherein the angle (α) is about 60°.

8. The connector of claim 1, wherein the conduit (3) exhibits a third portion (3c) in connection with the first longitudinal portion (3a) and the second longitudinal portion (3b) in order to allow fluid passage, the third portion (3c) terminating in a further inlet opening or outlet opening (11).

9. The connector of claim 1, wherein the main body (2) of the connector exhibits a shape corresponding to one of a group comprising:
- a T-shape,
- an X-shape,
- an H-shape,
- an S-shape,
- a Y-shape,
- a U-shape, and
- an L-shape.

10. The connector of claim 1, wherein the first longitudinal portion (3a) and the second longitudinal portion (3b) of the conduit (3) exhibit smooth surfaces (12), destined to couple to corresponding surfaces of a tubular port (7) in order to guarantee a fluid seal.

11. The connector of claim 1, wherein the protuberances (6) of the first longitudinal portion (3a) and the second longitudinal portion (3b) of the conduit (3) are destined to engage in corresponding parts of a tubular port (7), which tubular port (7) is at least partially counter-shaped to the protuberances (6), in order to guarantee a mechanical coupling between the connector and the tubular port (7).

12. The connector of claim 1, wherein the first longitudinal portion (3a) and the second longitudinal portion (3b) of the conduit (3) exhibit transversal sections of same geometry in order to enable connection between tubular ports (7) having same diameter.

13. The connector of claim 1, wherein the connector is entirely and exclusively made of an elastomeric material.

14. The connector of claim 13, wherein the elastomeric material is silicone.

15. The connector of claim 1, wherein the connector is made in a single piece by moulding.

16. A hydraulic circuit comprising:
- a plurality of hydraulic connectors (1) of the type according to claim 1;
- a plurality of hydraulic components each having at least a tubular port (7) engaging one of the connectors (1).

17. The hydraulic circuit of claim 16, wherein the tubular port (7) engaged to the respective connector (1) exhibits recesses (13) engaging corresponding protuberances (6) of the main body (2).

18. The hydraulic circuit of claim 16, wherein one of the hydraulic components exhibits a tubular port (7) having a longitudinal axis which does not coincide with a tubular port (7) of a second component, the tubular ports (7) being hydraulically connected by one of the hydraulic connectors (1).

19. The hydraulic circuit of claim 16, wherein the hydraulic components comprise one or more of components belonging to a group comprising:
- a valve,
- a pump,
- a tube,
- a sensor of a fluid characteristic,
- an ultrafilter,
- a blood treatment unit,
- a fluid collection reservoir.

20. A machine for extracorporeal blood treatment, comprising: a unit for extracorporeal treatment of blood (23);
- at least a section (20) for preparation of a treatment fluid, the preparation section (20) including a hydraulic circuit (100) of the type according to claim 16 conveying the treatment fluid to an inlet port (22) of the unit for extracorporeal treatment of blood (23);
- at least a section (21) destined for discharging the used treatment fluid, the discharge section (21) comprising a hydraulic circuit (100) of the type according to claim 16 conveying used treatment fluid from an outlet port (24) of the unit for extracorporeal treatment of blood (23) to the discharge.

21. The hydraulic circuit of claim 16, wherein the hydraulic circuit is a hydraulic circuit for machines for extracorporeal blood treatment.

* * * * *